US009095833B2

(12) United States Patent
Demmitt

(10) Patent No.: US 9,095,833 B2
(45) Date of Patent: Aug. 4, 2015

(54) SYSTEM FOR PERFORMING AUTOMATED SOLID PHASE EXTRACTIONS

(71) Applicant: Biolytic Lab Performance, Inc., Fremont, CA (US)

(72) Inventor: Thomas J. Demmitt, Fremont, CA (US)

(73) Assignee: Biolytic Lab Performance, Inc., Fremont, CA (US)

( * ) Notice: Subject to any disclaimer, the term of this patent is extended or adjusted under 35 U.S.C. 154(b) by 19 days.

(21) Appl. No.: 13/907,520

(22) Filed: May 31, 2013

(65) Prior Publication Data

US 2013/0323138 A1 Dec. 5, 2013

Related U.S. Application Data

(60) Provisional application No. 61/653,995, filed on May 31, 2012.

(51) Int. Cl.
| | |
|---|---|
| G01N 35/00 | (2006.01) |
| G01N 35/10 | (2006.01) |
| B01L 3/02 | (2006.01) |
| B01L 3/00 | (2006.01) |
| B01J 19/00 | (2006.01) |
| G01N 35/04 | (2006.01) |

(Continued)

(52) U.S. Cl.
CPC .......... *B01J 19/0053* (2013.01); *B01J 19/0046* (2013.01); *B01J 2219/0036* (2013.01); *B01J 2219/00315* (2013.01); *B01J 2219/00369* (2013.01); *B01J 2219/00376* (2013.01); *B01J 2219/00466* (2013.01); *B01J 2219/00509* (2013.01); *B01J 2219/00585* (2013.01); *B01J 2219/00596* (2013.01); *B01J 2219/00691* (2013.01); *B01J 2219/00722* (2013.01); *B01J 2219/00759* (2013.01); *B01L 3/0293* (2013.01); *B01L 3/563* (2013.01); *B01L 9/523* (2013.01); *B01L 2200/0605* (2013.01); *G01N 1/405* (2013.01); *G01N 35/028* (2013.01); *G01N 35/04* (2013.01); *G01N 35/1011* (2013.01); *G01N 35/1016* (2013.01); *G01N 35/1065* (2013.01); *G01N 35/1074* (2013.01); *G01N 2030/009* (2013.01); *G01N 2035/00237* (2013.01); *G01N 2035/1034* (2013.01); *G01N 2035/1039* (2013.01)

(58) Field of Classification Search
USPC ........................................................ 422/242
See application file for complete search history.

(56) References Cited

U.S. PATENT DOCUMENTS

| | | |
|---|---|---|
| 4,681,742 A | 7/1987 | Johnson et al. |
| 4,990,075 A | 2/1991 | Wogoman |

(Continued)

*Primary Examiner* — Jennifer Wecker
(74) *Attorney, Agent, or Firm* — Thomas Schneck; David Schneck

(57) ABSTRACT

The invention provides an improved instrument for automation of solid phase extraction chemistries typically used in biotechnology labs. The instrument includes a mechanism for transferring samples dissolved in a liquid from initial containers to reaction columns that are used to perform solid phase extractions. Samples, reaction columns and collection containers are in microtiter plate format or tubes that are on 18 millimeter centers. The transfer system is automatically cleaned after use in preparation for the next use. A dispense manifold is used to dispense various reagents into the reaction columns. Pressure differential is used to move reagents through reaction columns. A sliding cover is used to divert the reagent exiting reaction columns to waste or allowing collection of sample as it exits outlets of reaction columns. Samples are automatically collected in microtiter plates or in individual tubes or vials.

6 Claims, 20 Drawing Sheets

(51) Int. Cl.
*B01L 9/00* (2006.01)
*G01N 35/02* (2006.01)
*G01N 1/40* (2006.01)
*G01N 30/00* (2006.01)

(56) References Cited

U.S. PATENT DOCUMENTS

| | | | |
|---|---|---|---|
| 5,006,309 A | 4/1991 | Khalil et al. | |
| 6,083,763 A * | 7/2000 | Balch | 506/9 |
| 6,117,396 A | 9/2000 | Demers | |
| 6,303,387 B1 | 10/2001 | Birch et al. | |
| 6,485,690 B1 | 11/2002 | Pfost et al. | |
| 6,818,060 B2 * | 11/2004 | Stewart et al. | 117/68 |
| 7,488,604 B2 | 2/2009 | Clark et al. | |
| 7,713,708 B2 | 5/2010 | Roback et al. | |
| 2001/0055801 A1 | 12/2001 | Chen et al. | |
| 2002/0009391 A1 * | 1/2002 | Marquiss et al. | 422/63 |
| 2003/0032925 A1 * | 2/2003 | Stone | 604/191 |
| 2003/0143725 A1 * | 7/2003 | Chen et al. | 435/287.2 |
| 2004/0166022 A1 * | 8/2004 | Barzilai et al. | 422/63 |
| 2005/0070848 A1 * | 3/2005 | Kim et al. | 604/140 |
| 2005/0194318 A1 | 9/2005 | Ozbal et al. | |
| 2006/0002824 A1 * | 1/2006 | Chang et al. | 422/100 |
| 2008/0003147 A1 * | 1/2008 | Miller et al. | 422/100 |
| 2008/0038713 A1 | 2/2008 | Gao et al. | |
| 2009/0181463 A1 | 7/2009 | Chen | |
| 2011/0015091 A1 | 1/2011 | Glezer et al. | |
| 2011/0110180 A1 * | 5/2011 | Snider et al. | 366/142 |

* cited by examiner

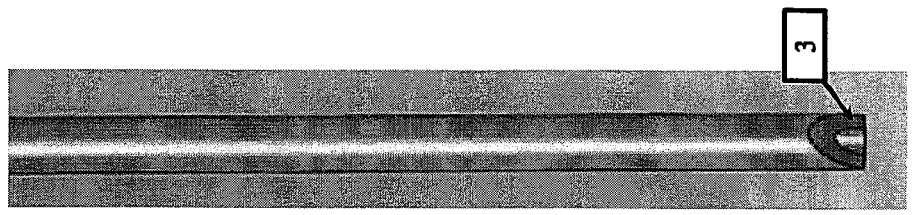
Figure 4c — Pickup Tube hole after cuts
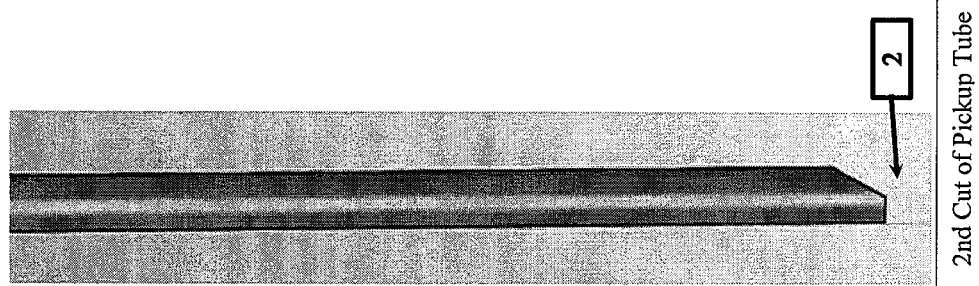
Figure 4b — 2nd Cut of Pickup Tube
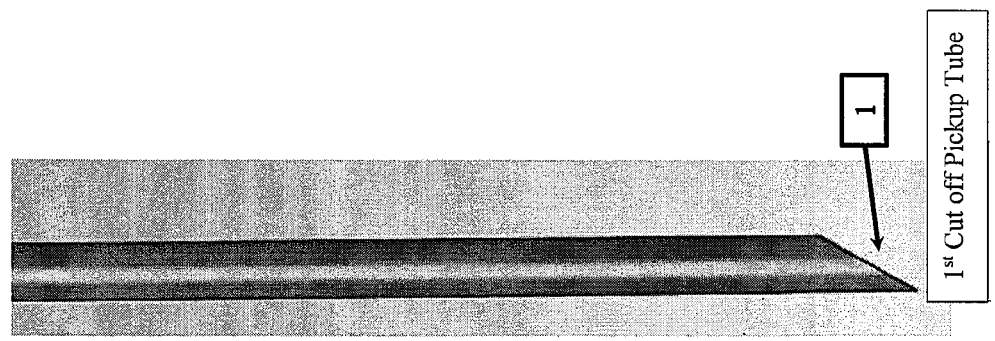
Figure 4a — 1st Cut off Pickup Tube

SYSTEM FOR PERFORMING AUTOMATED SOLID PHASE EXTRACTIONS

CROSS-RELATED TO PATENT APPLICATION

This applications claims priority from provisional application serial no. 61/653,995, filed May 31, 2012.

TECHNICAL FIELD

This invention relates to automated chemistry instrument and more specifically methods and instrumentation for automated solid phase extractions of biomolecules.

BACKGROUND

Solid phase extraction of biomolecules is a required final step in biomolecule synthesis. The instrumentation used to perform the solid phase extractions has traditionally been either manual or using expensive robotic systems. As solid phase synthesis of small molecules such as oligonucleotides and peptides has proliferated, the need for low cost purification and solid phase extraction of these small molecules has also grown. An economical automated system that will perform various solid phase extraction chemistries automatically is needed. This system must perform these chemistries on samples that are in a multi-well plate format or in individual vials that can be placed on 18 millimeter centers.

It is apparent that a lower cost, fully automated system is needed by the industry. In such an instrument it is preferred to transfer of samples using cleanable, reusable mechanisms that do not result in cross contamination between samples in the same run. In addition, this mechanism should not result in carryover contamination from samples in a previous run to the samples in the current run.

The instrument must also have a reasonably economical system for dispensing reagents into a multitude of reaction columns. In addition, the system must be able to collect the desired product in individual tubes or wells without cross contamination between the individual samples being collected.

SUMMARY

Considered broadly, automated solid phase extraction instruments, are of the type that utilize flow through reaction columns with an open top for introduction of samples and reagents into the reaction column and an open bottom for removal of waste reagents from the reaction columns. Specific properties of material contained within reaction columns are chosen by the user to perform the particular solid phase extraction they desire to perform. For purposes of this system, a variety of reaction columns may be utilized. The system is designed to be flexible making it suitable for use with reaction columns generally found in scientific labs.

Pressure differential across the reaction columns is used to move samples and reagents through the reaction columns. Reagents, buffers and samples exiting the outlets of the reaction columns may be sent to waste or collected in containers (collect containers). A transfer subsystem is used to transfer liquid samples from a sample container that may contain up to 96 individual samples simultaneously to a similar number of reaction columns. There is one reaction column per sample therefore one may have up to as many as 96 reaction columns. Transfer of the entire volume of each sample is usually required. However reaction columns may not have enough space to contain the entire volume of each sample therefore the system is capable of transferring the sample multiple times. Between each transfer the sample system will expel the liquid buffer out of the reaction column outlets to waste while retaining the sample within the reaction column. This process is repeated until the desired volume of the samples have been transferred to the reaction columns. The system used to accomplish this process is a novel system that consists of a sealable chamber that contains the sample containers, PEEK pickup tubes that extend into the bottoms of the sample containers, and a spring loaded platform that pushes the sample containers up so that the PEEK pickup tubes reach the bottom of the sample containers. The PEEK pickup tubes may be cut so that the end can pick up the entire volume of each liquid sample. The cut end is cut on a 60 degree angle and 0.050 inch long tip of angle is cut off so that ½ of the hole in PEEK pickup tubes is pressed flat against the bottom of sample containers and ½ of the opening of the hole in PEEK pickup tube is open to the liquid sample on the 60 degree angle. This cut ensures that all the liquid will be transferred and that PEEK pickup tubes will not be plugged by pressing against the bottom of the sample containers. PEEK pickup tubes are maintained straight so that they are guided into the sample containers by a guide plate that follows the tubes as the tubes and the tube manifold are moved up to open the sealable chamber to allow access to the sample container. The PEEK tubes are coupled to Teflon tubes at the tube manifold. Both the PEEK tubes and the Teflon tubes are 1/16 inch OD×0.030 inch ID. The coupling of these two tubes is accomplished using ferrules and tube nuts designed for coupling tubes together. The Teflon tubes are about 18 inches long and terminate in a pattern that matches the pattern of reaction columns being used. The dispense ends of the Teflon tubes have PEEK tubes inserted into them. The PEEK tubes are held in place and sealed to the inside of the Teflon tubes by standard tube ferrules. The ID of the PEEK tubes is 0.015 inch. This smaller diameter provides back pressure which facilitates complete transfer of all samples even when some transfer tubes are not transferring any sample. The exposed ends of the PEEK tubes are formed at a 45 degree angle which is used to eliminate splashing as the liquid samples are transferred. A mechanism controlled by pneumatic cylinders lowers the angled tips of the PEEK tubes into the top of the reaction columns during the transfer process to contain atomized droplet of sample containing liquid within each reaction column.

Pickup ends of PEEK pickup tubes and inside bottom of sample transfer containers are lower than the dispense nozzles on the dispense ends of the transfer tube assembly. This arrangement ensures that any sample buffer that is remaining in the transfer tubes at the time the transfer is siphoned back into the transfer containers so that drops do not form on the ends of the transfer tube dispense nozzles. Drops forming on the dispense ends of the transfer tubes could fall off into incorrect reaction columns in the process of the system controller moving reaction columns from the transfer station to the reaction station.

The transfer tube pickup manifold also contains a unique mechanism for washing the PEEK pickup tubes between uses. The washing system consists of horizontal passages drilled through the manifold such that the horizontal passages intersect the vertical holes that the PEEK tubes go through. One long horizontal passage is drilled the width of the manifold such that it intersects 8 PEEK pickup tubes. The horizontal passage is drilled offset such that the center of the horizontal passage intersects the edge of the vertical holes. The horizontal passage is located vertically so that it is just below the sealing ferrules that are attached to the top end of each PEEK pickup tube. Each horizontal passage is connected to a tube which is in turn connected to a solenoid valve. The other side of the solenoid valve is connected to a tube which is connected to a pressurized bottle of wash buffer. When the solenoid valves are opened the wash buffer flows into the transfer tube pickup manifold filing the horizontal passage. Wash buffer flows between the OD of the PEEK pickup tubes and the ID of stainless steel outer tubes. Wash buffer exits the space between the PEEK pickup tubes and outer stainless steel tubes and down the outside of each PEEK tube washing it and filling each sample container with wash buffer. The sealable sample chamber can then be pressurized to push the wash buffer through the transfer tubes to waste thereby washing the outside and the inside of the transfer tube assemblies.

A distribution manifold is used to dispense various liquid reagents and buffers into the open tops of the reaction columns to facilitate each chemistry step needed for the particular solid phase extraction being performed. Reagents are selected to be dispensed by the reagent distribution manifold using 2 way valves. The dispensing distribution manifold uses 12 each 2 way valves to dispense reagents into individual reaction columns. The distribution manifold is capable of dispensing reagent into up to 96 individual reaction columns without relative motion between dispensing nozzles and reaction columns.

Reaction columns are contained within a holder whose position can be selected by the system controller. When the holder containing the reaction vessels is positioned below the reagent dispense nozzles the reaction vessels are contained within a chamber whose pressure is controlled by the system controller. After reagents are dispensed into the reaction columns the system controller selects a pressure to apply to the reaction columns based on the protocol. A lower pressure is applied to slowly move reagents through the reaction columns. A higher pressure is applied to move reagent quickly through the reaction columns or to completely empty the reaction columns. Low and High pressures may be set using standard pressure regulators. The exact pressure chosen is dependent on the flow properties of the reaction columns. Pressures typically range from 2 psi to 12 psi.

A mechanism is used to send the effluent exiting the outlets of reaction columns either to waste or to collection containers. This unique mechanism consists of a specially designed sliding cover that is located below the outlets of the reaction columns and above the inlets of the collection containers. The design of the sliding cover is such that waste liquid that lands on the cover is shed off the front and rear but not the left and right ends. The design is further enhanced by extensions that protrude downward on the front and rear past the tops of the collection containers. This is important to ensure that no waste ever gets into the collect containers. The sliding cover top is an angle that slopes to the front and rear. The left and right of the cover have troughs cut so that liquid reagent cannot flow off the left and right sides of the cover. The front and rear of the cover have extensions that extend down past the tops of the collect containers so that any waste reagent flowing off the front or rear of the cover does not depart the cover until it is below the open tops of the collect containers.

BRIEF DESCRIPTION OF THE DRAWINGS

FIG. 4a is a side view of the first cut of the pickup tube.
FIG. 4b is a side view of the second cut of the pick-up tube.
FIG. 4c is a side view of FIG. 4b, with pickup tube rotated ninety degrees.

DETAILED DESCRIPTION

One embodiment of the system for performing automated, solid phase extraction is an automatic system controlled by a suitable controller and software. Software is written to allow users to use this system to duplicate the processes of solid phase extraction as developed by the providers of the solid phase extraction reaction columns.

Figure 1:
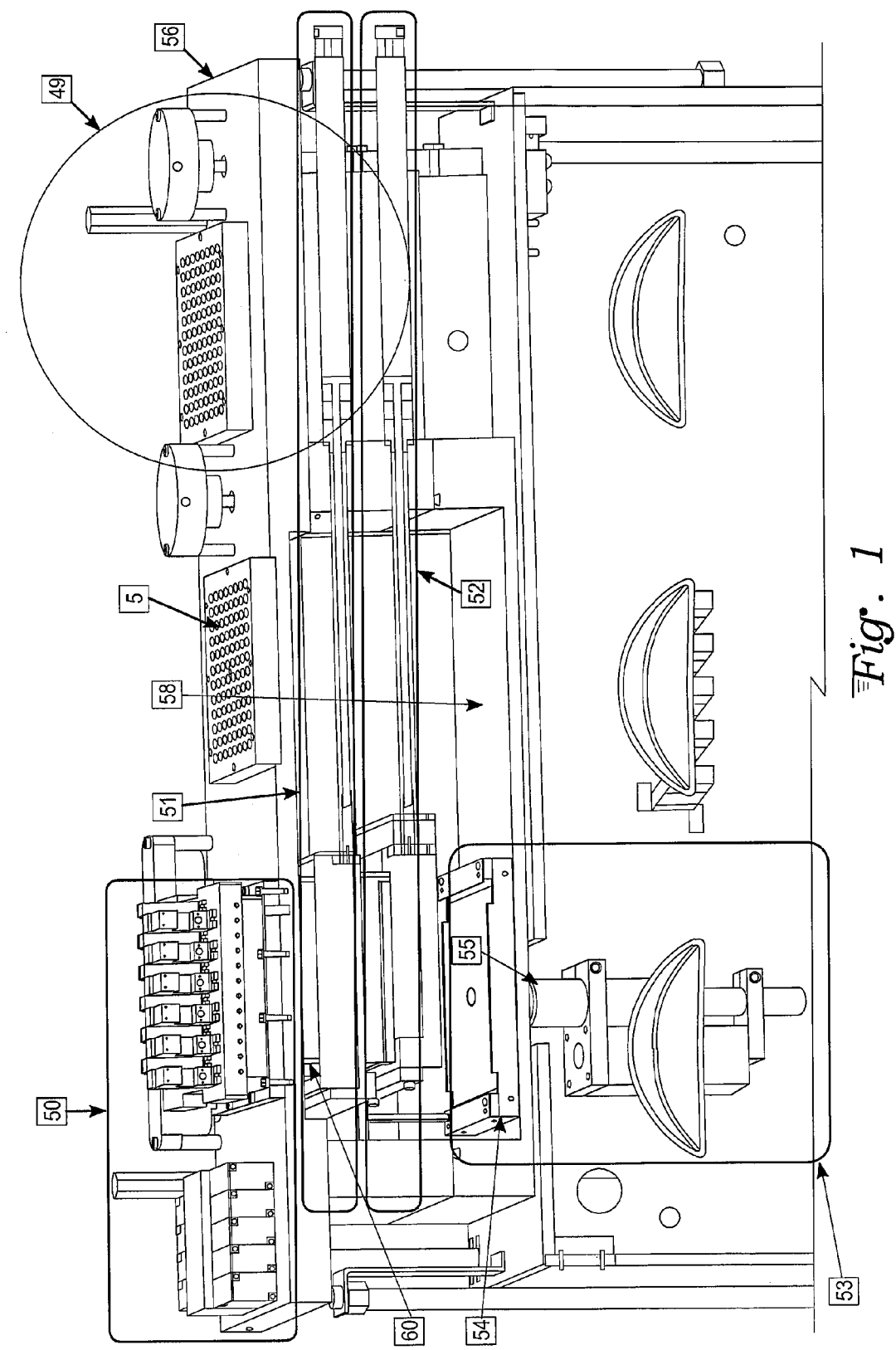
FIG. 1 is a front perspective view of the automated system.

With reference to FIG. 1, an embodiment of a system for performing automated solid phase extractions is illustrated. This system includes a transfer system 49 suitable for transfer of samples from a multi-well storage plate or storage tubes to dispense nozzles at an underside of dispense nozzle spacing plate 5. The spacing pates are mounted on bench 56. A dispense System 50 allows various reagents to be dispensed through an array of reaction columns. Reaction column shuttle 51 provides movement of the reaction column array between the transfer system and the dispense system. The cover and cover shuttle 52 allows the liquid dispensed by the dispense system through an array of reaction columns to be diverted to waste rather than be collected in the collection plate. Finally, the collection plate system 53 includes a collection plate lift 54 and a pneumatic cylinder 55 for positioning the collection plate.

Figure 2:
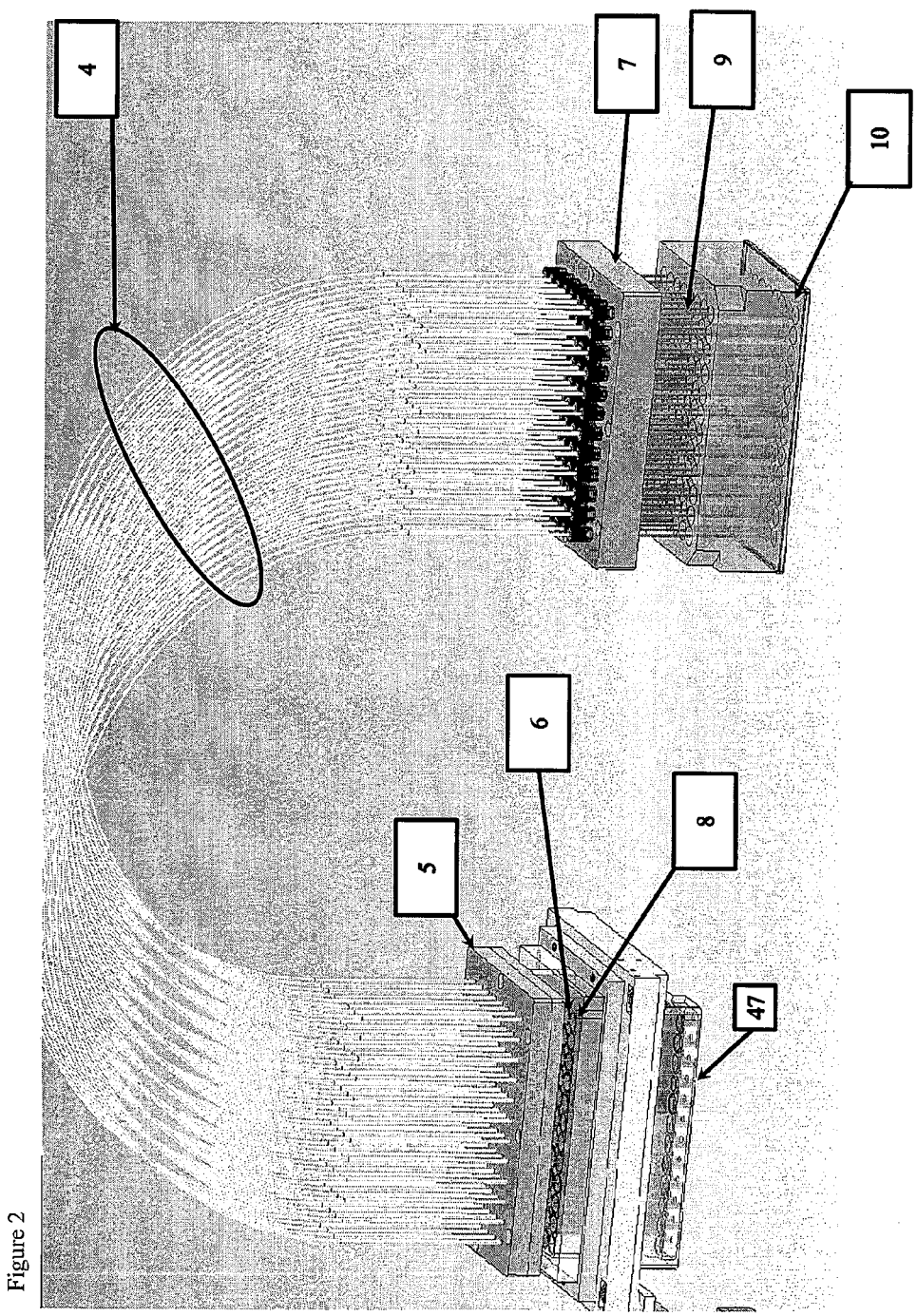
FIG. 2 is a front perspective view of the transfer subsystem.

With reference to FIG. 2, a liquid transfer system allows for transferring liquid samples from the wells of a sample container 10 containing an array of as many as 96 individual containers to a similar matrix of reaction columns 8. Pickup tube manifold 7 holds an array of equally spaced pickup tubes 9. A spring based lift allows a sample holding container 10 to be lifted into a position in which the pickup tubes each extend into one of the sample holding wells or tubes. A pressure head is introduced that drives the liquid into pickup tubes 9 and into transfer tubes 4. At the opposing end of transfer tubes 4 are dispense nozzle array 6 directing liquid into the reaction columns 8. A nozzle plate 5 allows the nozzles to be mounted with a fixed spacing.

Figure 3:
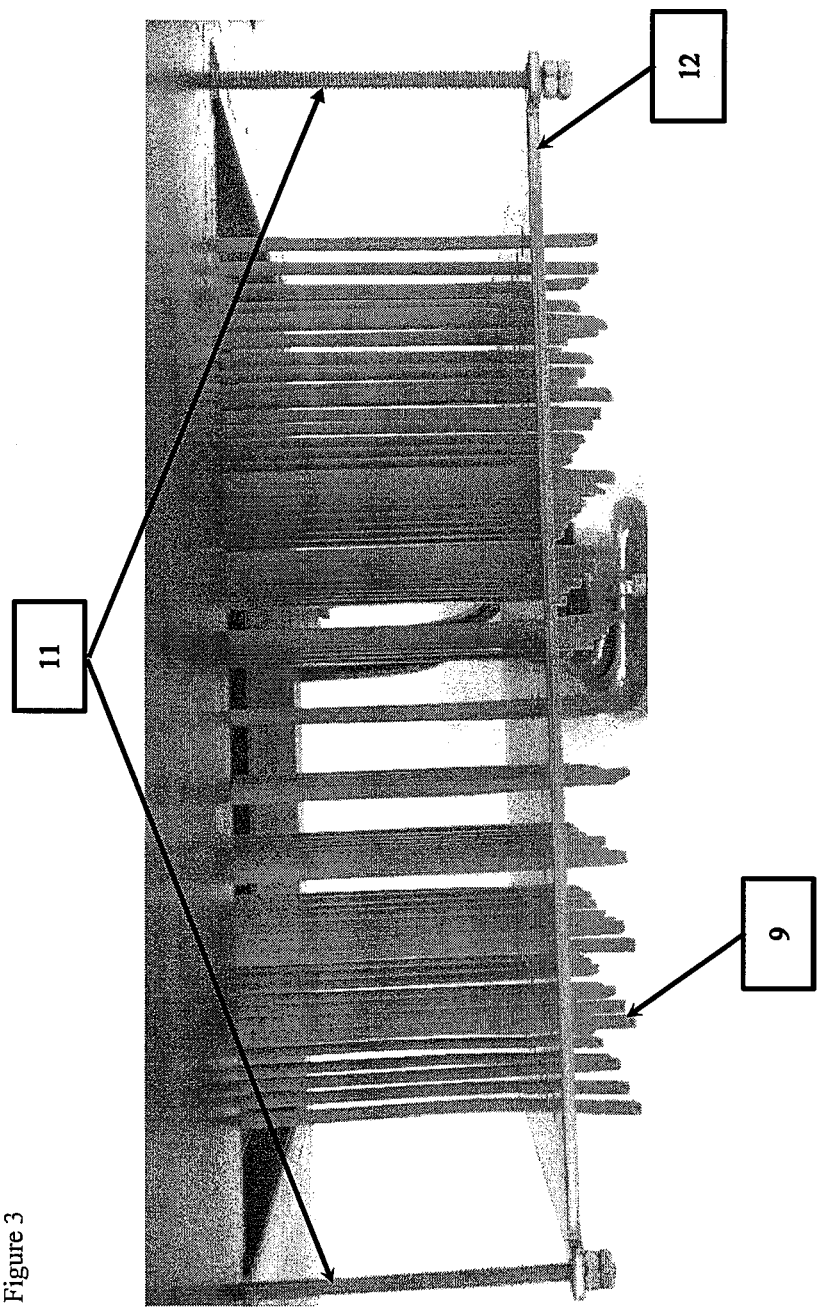
FIG. 3 is a front perspective view of PEEK pickup tubes with guide plate for keeping tubes in alignment with the sample container matrix.

With reference to FIG. 3, to maintain the spacing of the pickup tubes, a movable guide plate 12 slides up and down on fixed rods 11. This guide plate contains ninety six holes in which PEEK pickup tubes 9 pass through maintaining correct alignment such that PEEK pickup tubes 9 are guided into sample transfer containers.

With reference to FIGS. 4a, 4b, 4c, the ends of the pickup tube is shown. Details of this embodiment for transferring liquid samples from a matrix of ninety six sample transfer containers to a similar matrix of reaction columns includes a PEEK pickup transfer tubes which have the pickup end cut to a 60 degree angle 1, followed by a second cut in which 0.050 inch from the tip of said angle is cut off 2 (see FIG. 4b) providing a tube end 3 (FIG. 4c) with an opening. If the tube end is pressed onto the flat surface of a plate well bottom, the sample is still able to enter the tube.

Figure 5:
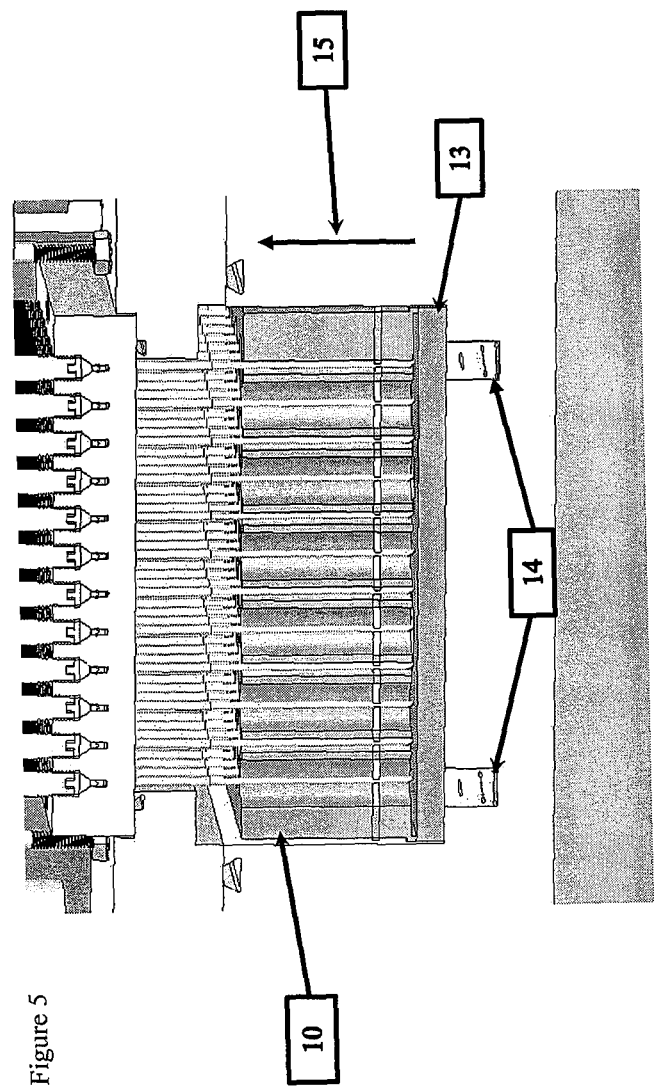
FIG. 5 is a side perspective view of the spring loaded platform that pushes sample transfer containers up so that sample transfer container inside bottom hits tip of PEEK pickup tubes.

With reference to FIG. 5, the transfer system also includes a provision for transferring the entire contents of each sample transfer container 10 which includes a movable sample support plate 13 located under the sample transfer container. Four springs 14 are positioned under the movable support plate 13. These springs 14 push said support plate 13 up (as indicated by arrow 15), thereby pushing up said sample transfer container 10 until PEEK pickup tubes 9 touch inside bottom of said sample transfer container 10.

Figure 6:
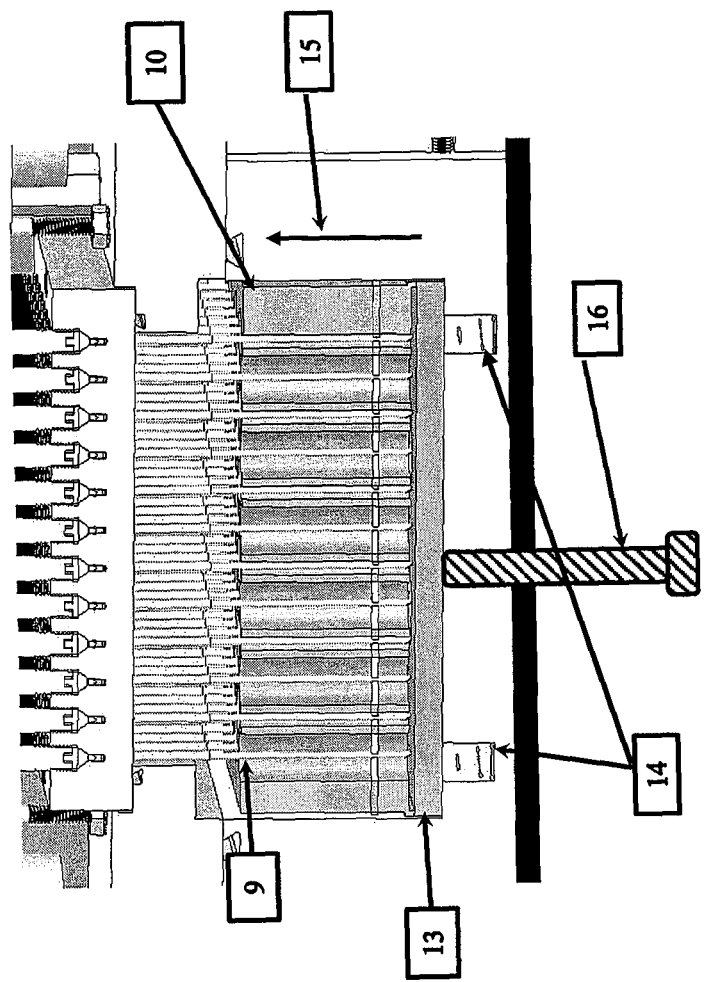
FIG. 6 is a side perspective view of the spring loaded platform height restriction device to limit the volume of sample transferred, shown with transfer tubes and sample container.

With respect to FIG. 6, if the user requires a sample transfer of less than the entire volume contained in said sample container 10 limit screw 16 is used to limit the height said sample container 10 can move up thereby limiting the depth said PEEK pickup tubes 9 are immersed into liquid sample.

Figure 7:
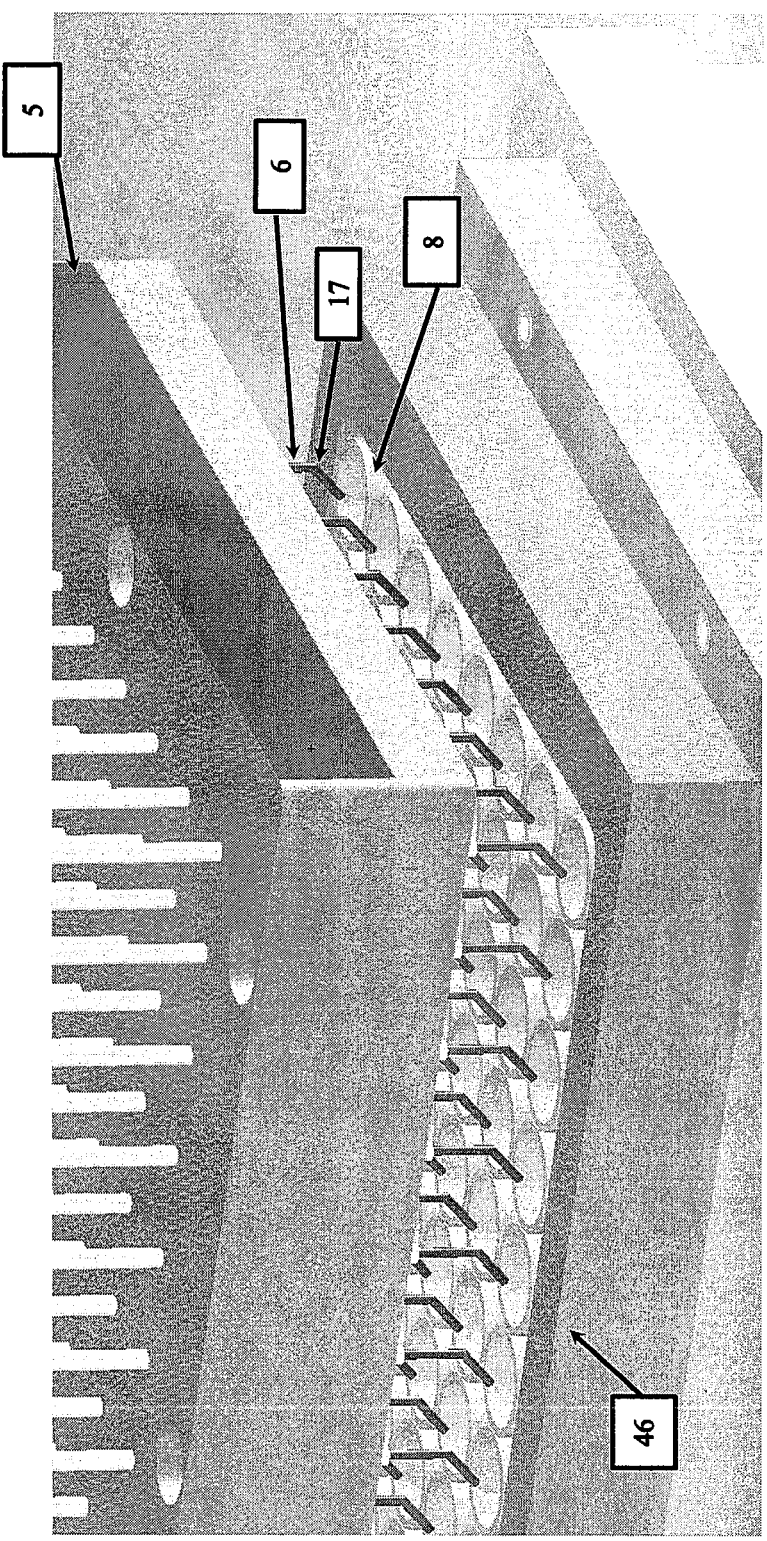
FIG. 7 is a side perspective view of the dispense ends of the transfer tube assemblies relative to reaction column inlets.

With respect to FIG. 7, a dispense nozzle spacing plate 5 spaces dispense nozzles 6 over reaction columns 8. Reaction columns are held in reaction column holder 46.

Figure 8:
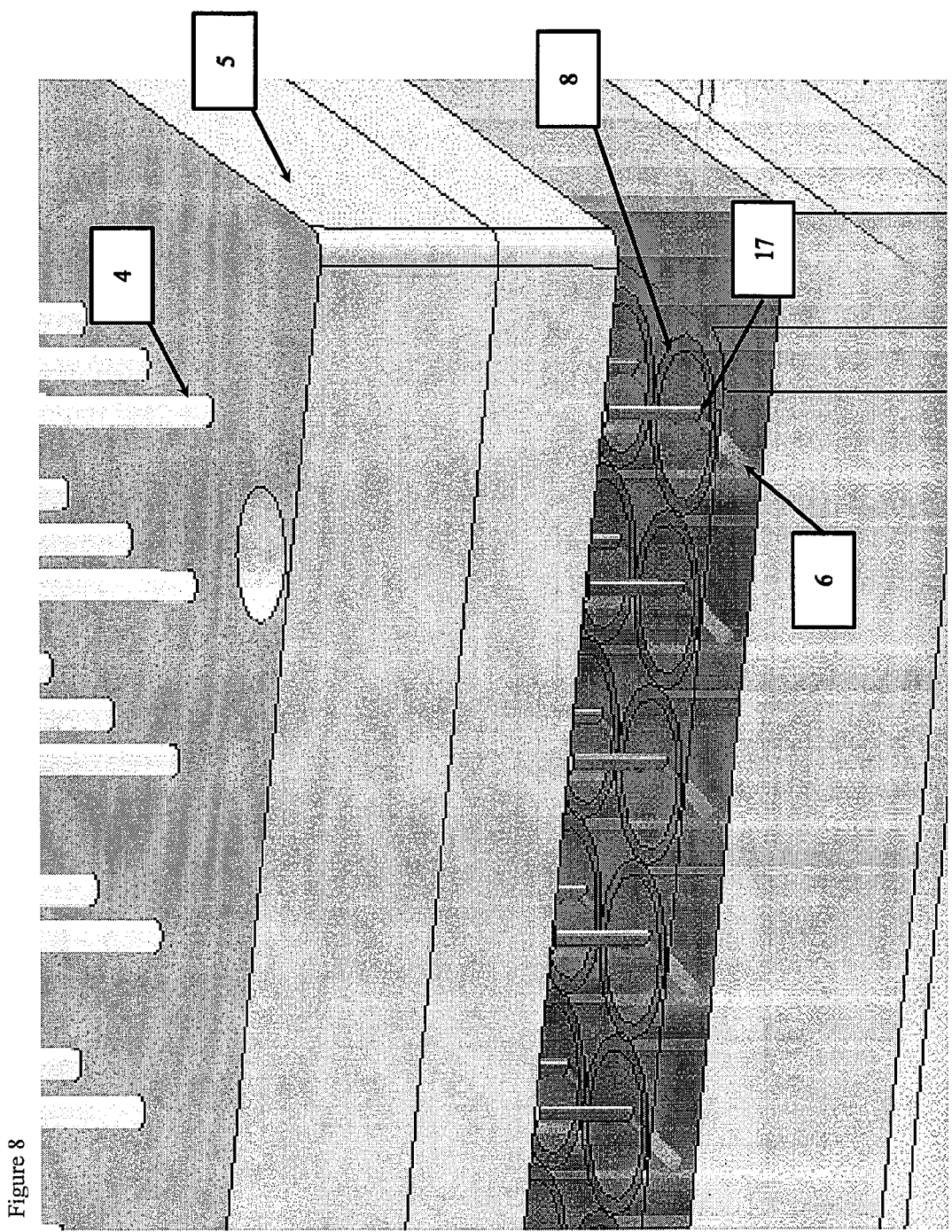
FIG. 8 is a side perspective view of the ends of the dispense nozzles extending into the reaction columns.

With respect to FIG. 8, the sample transfer tube enters dispense nozzle spacing plate 5, where dispense nozzles 6 are directed onto reaction column 8. The reaction columns are filled with a porous material that is used to perform the solid phase extraction (separation). This material severely restricts the flow of reagents through it. Therefore when liquid sample or other reagents are applied to the open top the liquid will stay in the reaction column for at least several minutes before it starts to drip out the bottom. Once liquid does move from the top of the reaction column to the bottom of the reaction column, the chemistry taking place as the liquid sample moves through the material in the reaction column extracts the oligo or peptide from the liquid and retain this until it is extracted.

The transfer dispense nozzle 6 has an angled tip 17 that directs the transferred liquid onto the side of reaction column 8. Liquid which is pressure driven through Teflon tube 4 to dispense end of transfer tube 4 out dispense nozzle 6. In this example, angled tip 17 is at a 45 degree angle. Liquid exiting tube 4 is directed onto the inside wall of the reaction columns 8 thereby retaining all fluid exiting each transfer dispense nozzle 6 within the corresponding reaction column.

Figure 9:
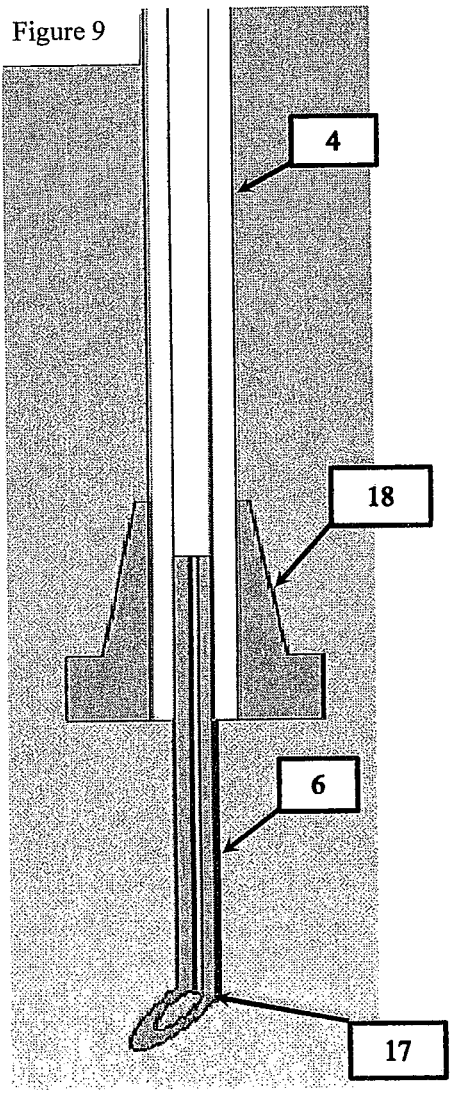
FIG. 9 is a cross sectional view of one transfer tube connected the pickup tube manifold on the right and showing a dispense nozzle on the left.

With reference to FIG. 9, a ferrule 18 retains dispense nozzle 6 on Teflon tube 4. Dispense nozzle 6 is shown having angled tip 17.

Figure 10:
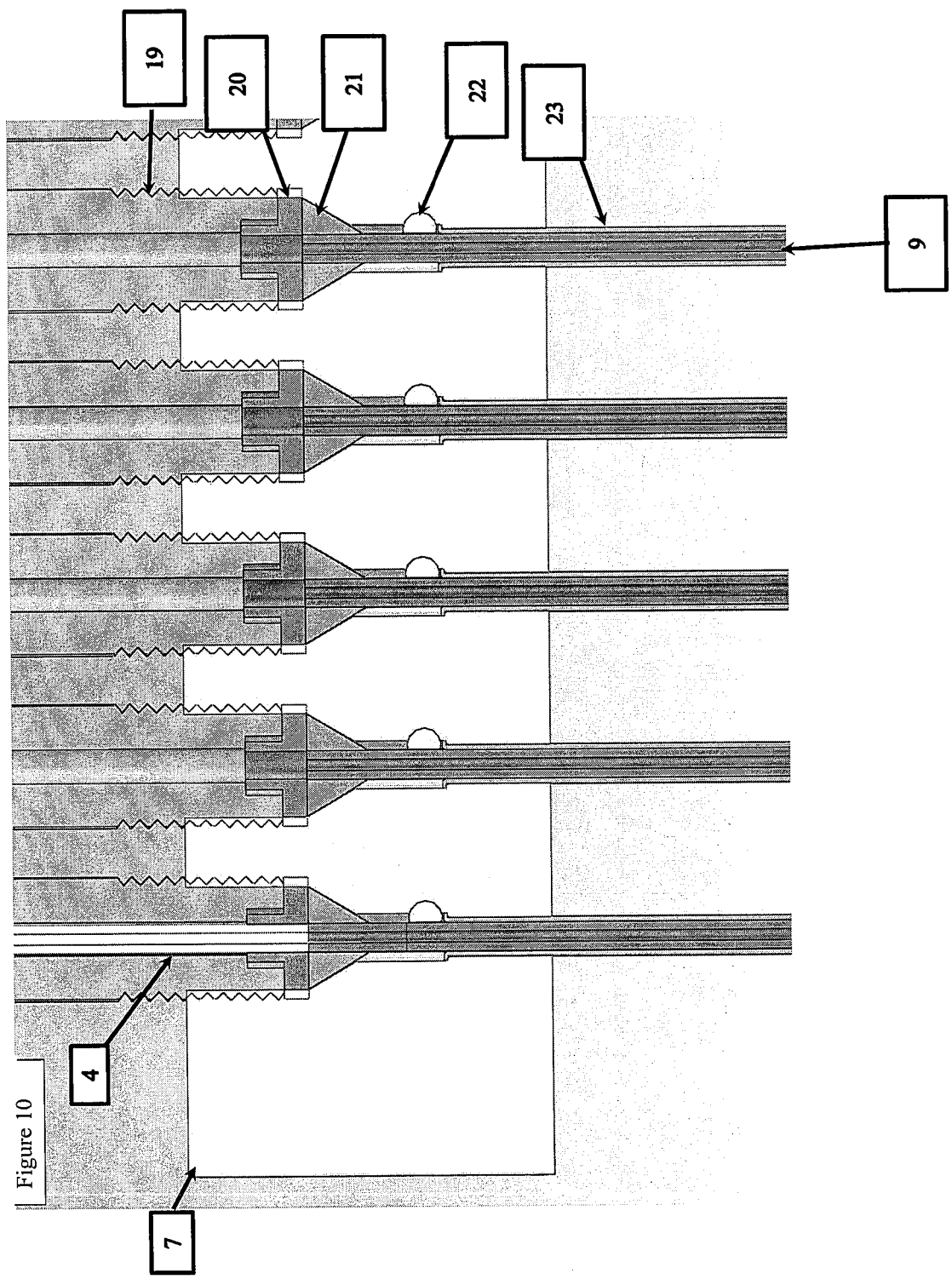
FIG. 10 is a cross sectional view of the PEEK pickup transfer tubes mounted in the transfer manifold detailing the pickup tube washing system.

An embodiment allowing for washing the transfer tubes automatically is detailed in FIG. 10. The transfer sample container is contained within a chamber that can be pressurized or vented through standard solenoid valves controlled by the system controller. In one embodiment, the sample transfer chamber is pressurized to a pressure of 9 psi for transferring samples. Pressure in the chamber forces liquid sample through the PEEK pickup tube 9 to the sample transfer pickup manifold 7. At manifold 7, the PEEK pickup tube 9 is coupled to a Teflon tube 4 via ferrule 21, ferrule 20 and tube nut 19. Teflon tube 4 is 1/16 inch OD×0.030 inch ID×18 inch long.

Figure 20:
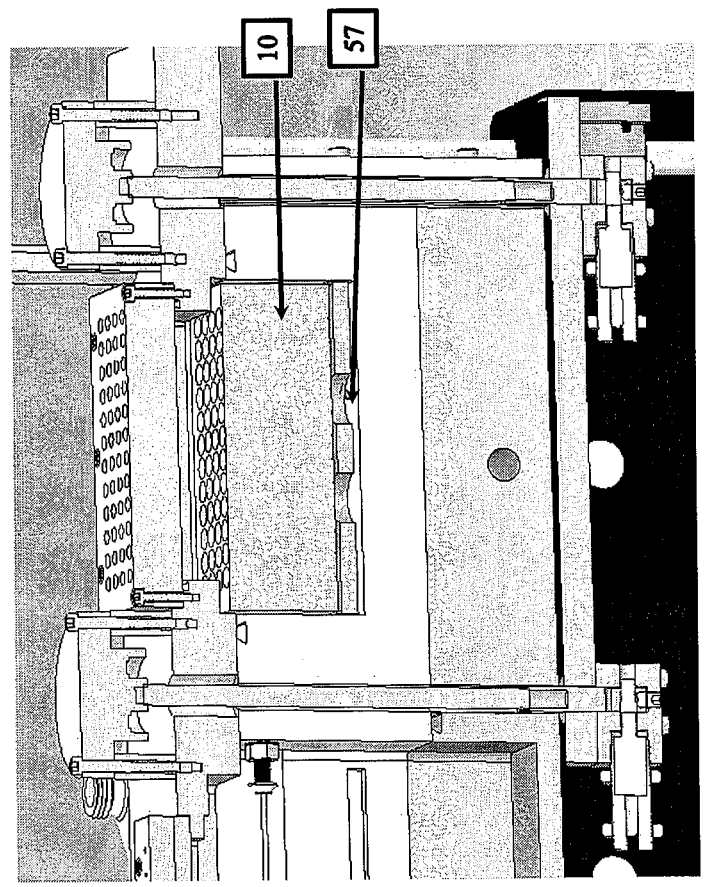
FIG. 20 is a cross section view of sample transfer chamber.

After sample is transferred through sample transfer tubes 4 to reaction columns 8, sample transfer tubes 4 must be cleaned before next use. In one embodiment, a method for cleaning sample transfer tubes 4 between uses is enabled by this system. Prior to cleaning of sample transfer tubes the system controller will move reaction columns to the left which is reagent flow and reaction position. Washing system is implemented through the mechanisms shown in FIG. 10. Each set of eight PEEK pickup tubes 9 has one wash buffer feed flow path 22. The wash buffer flow path 22 is 0.1 inch ID and it is located such that its center is tangent to the OD of PEEK pickup tubes 9. The position of said flow path 22 relative to said PEEK pickup tubes 9 allows free flow of wash buffer to eight PEEK pickup tubes 9 said flow path 22 encounters. A stainless steel guide 23 is installed in transfer manifold 7 for each PEEK pickup tube 9. ID of said guide 23 is 0.072 inch and OD of said PEEK pickup tube is 0.062 inch allowing a gap between them of 0.005 inch. Wash buffer is flowed through said passage 22 and flows between said PEEK Pickup tube 9 and said guide 23 then follows OD of said PEEK pickup tube 9 into transfer sample container 10 filling all sample containers in the array of sample containers with wash buffer wherein the system controller stops flow of wash buffer. System controller then seals the sample transfer pickup chamber and applies 9 psi pressure. Wash buffer is forced through the transfer tube assemblies 4 to waste. The pickup tube manifold is connected to a pressurized bottle of wash solution. As shown in FIG. 10, the wash solution flows into a channel 22 that supplies a row of pickup tubes. The wash solution moves down the space between the outer stainless steel jacket 23 and the inner PEEK tube, and into the sample holder wells. The wells fill, washing both the well and the outside of the transfer tube. The flow is stopped, pressure is then reapplied to the sample holder, driving the wash fluid into the pickup tubes 9, through the transfer tubes, and out the dispense nozzles 6. In FIG. 20 it can be seen that the space below the transfer dispense nozzles is an open space that is going to waste. There is a container below the transfer dispense nozzles that catch the waste and send it to an external waste container.

Figure 11:
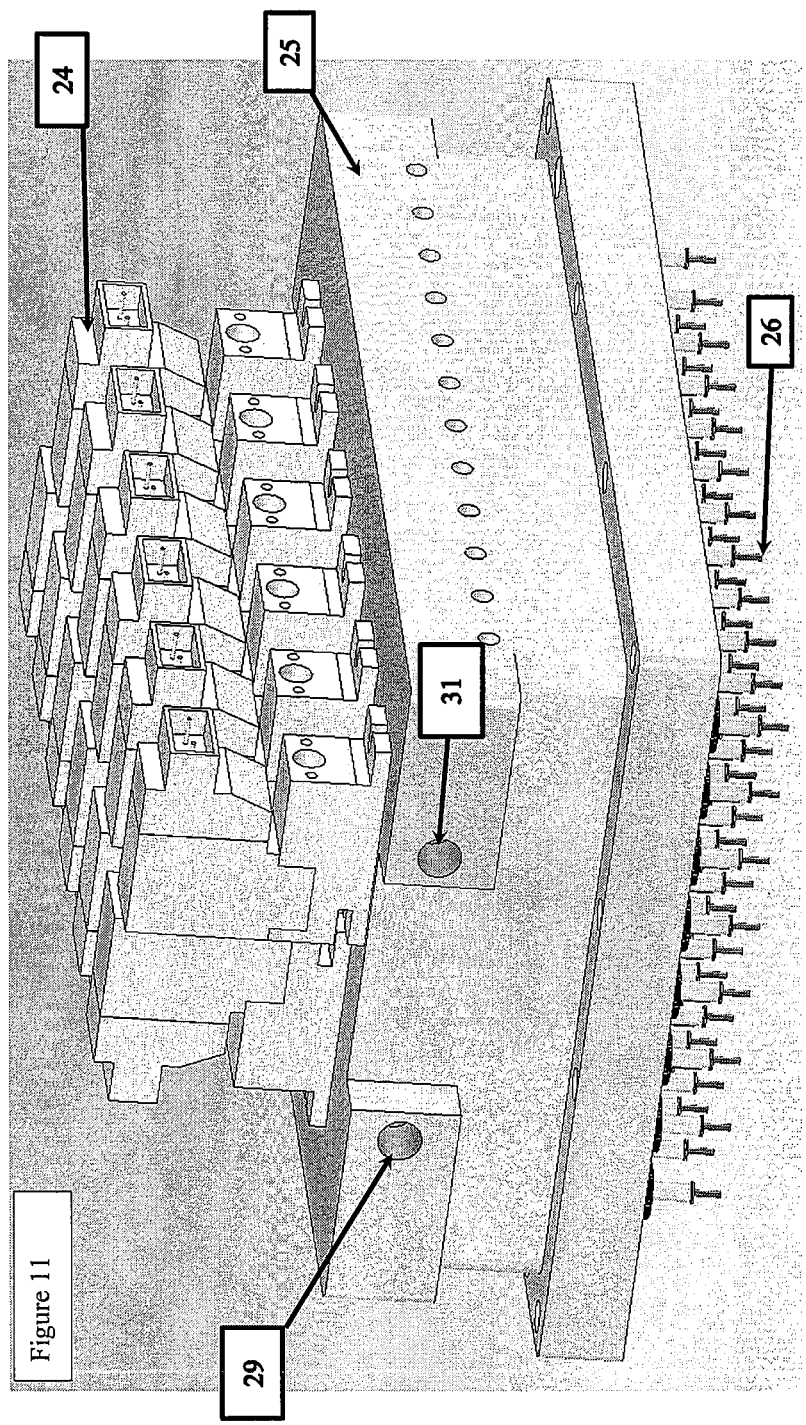
FIG. 11 is a side perspective view of the reagent dispensing manifold assembly.

In addition to the transfer subsystem, the system includes dispense and draining subsystem. After the samples have been transferred to the reaction columns, the reaction columns may be moved by shuttle 52 shown in FIG. 1 to a position below the dispense manifold 25. With reaction vessel holder 46 positioned below the reagent dispense manifold 25 a sealable chamber 60 is created at the tops (inlets) of the reaction vessels. With reaction columns positioned below reagent dispense manifold 25 various reagents can be directed from reagent dispense manifold 25 into the open tops of the reaction columns. With reference to FIG. 11, one embodiment utilizes manifold 25 shown in FIG. 11 for dispensing selectable reagents into as many as ninety six different reaction columns. This embodiment includes standard pressure driven reagent flow system for eight different reagents. The reagent storage and control part of the system is not shown as it is using standard pressurized bottles of reagents and solenoid valves and tubing which are in common use in the industry.

Figure 12:
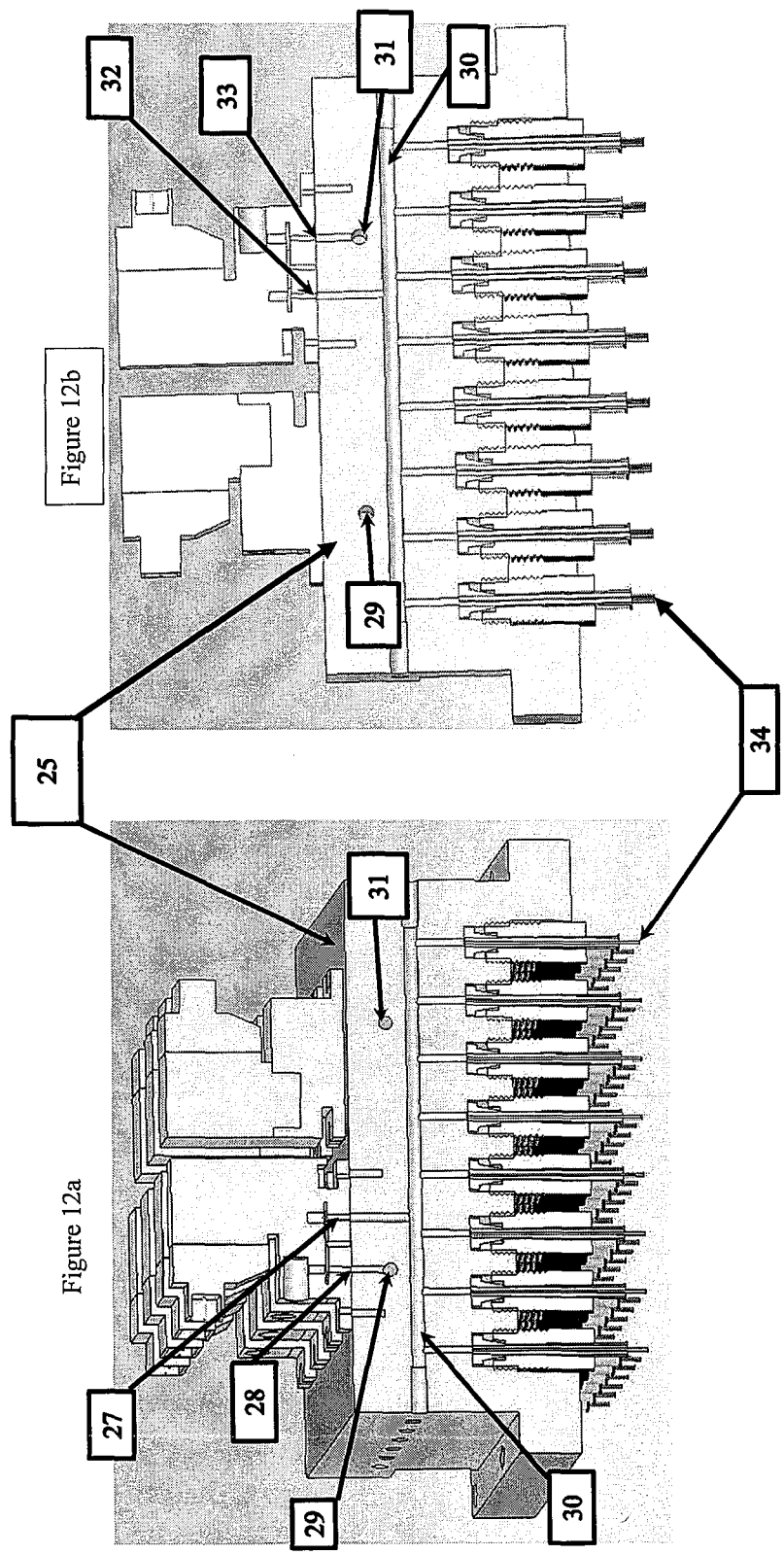
FIGS. 12a, 12b shows 2 cross section views of the reagent dispense manifold. The figure on the left shows the flow path for dispensing nozzles controlled by the 6 valves on the rear of the manifold while the figure on the right shows the flow path for the dispensing nozzles controlled by the 6 valves on the front of the manifold.
Figure 13:
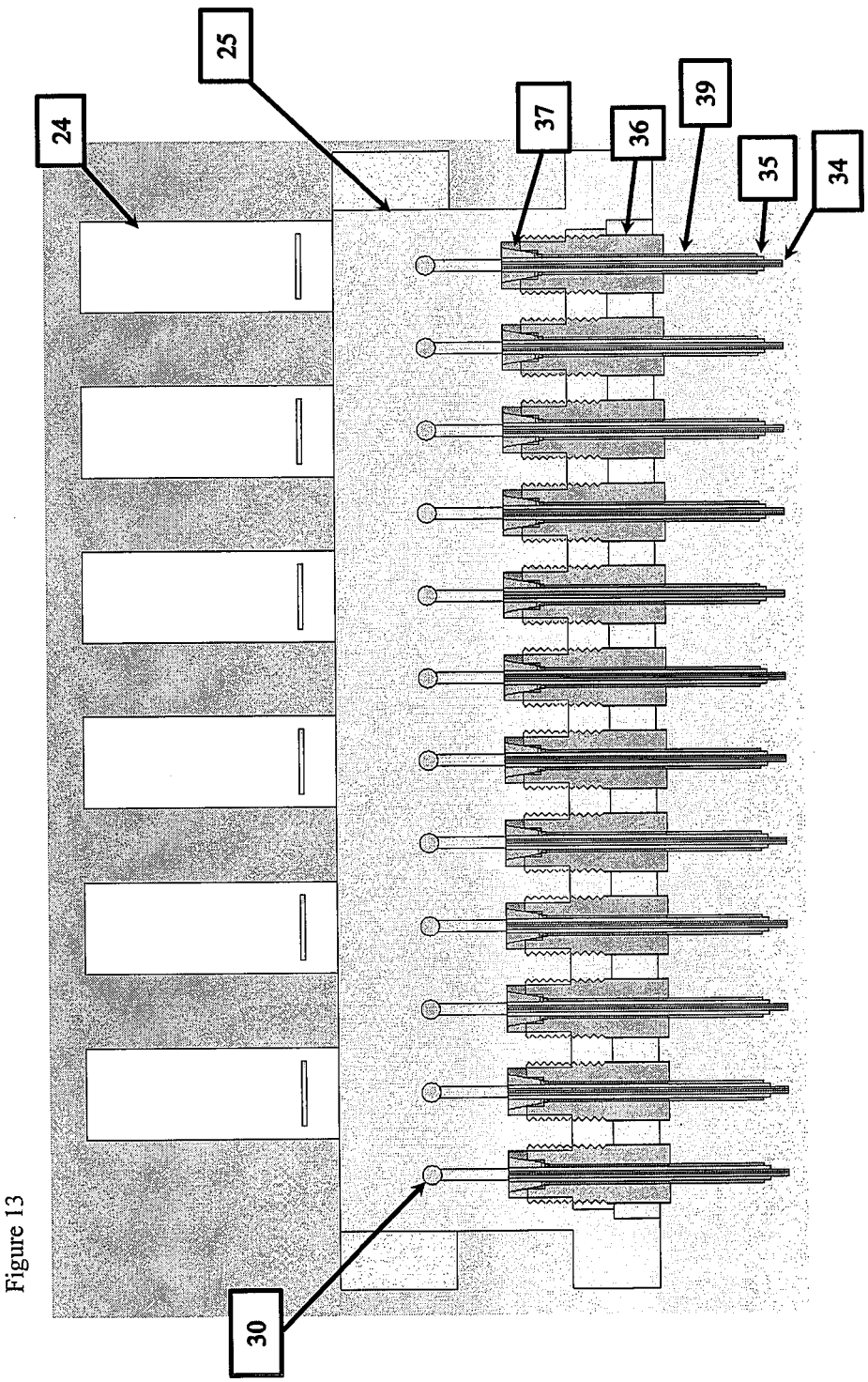
FIG. 13 is a cross section view of the dispense manifold showing the construction of the dispense nozzles.
Figure 14:
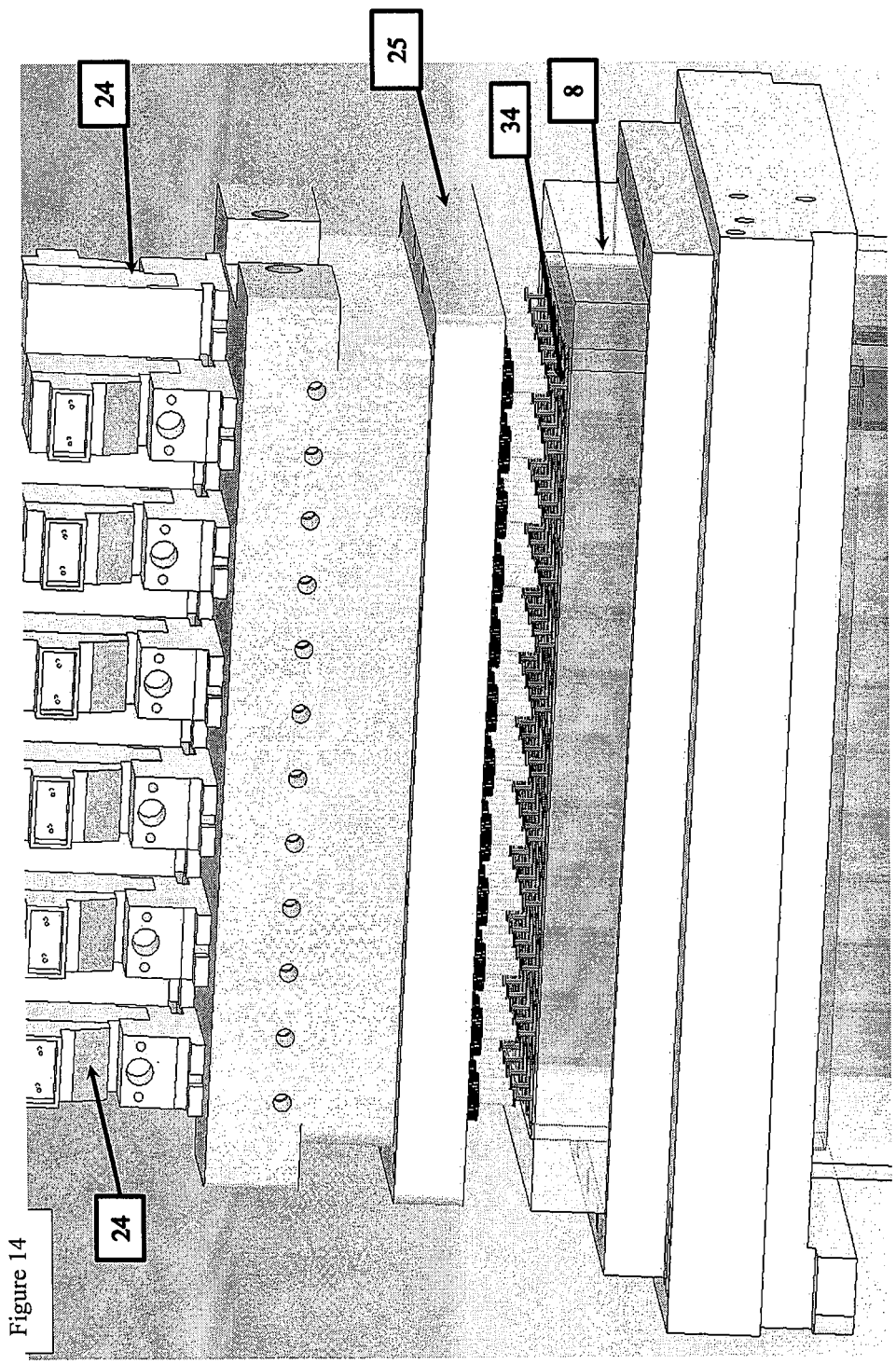
FIG. 14 is a side perspective view of the dispense manifold with dispense nozzles positioned over the reaction columns. Notice that the dispense nozzle tips protrude into the reaction columns slightly to avoid dispensing into adjacent reaction columns.

Manifold 25 shown in FIG. 11 for dispensing measured volumes of reagents into a matrix of open top columns is embodied in the system. Reagents are driven into manifold 25 via two ports and flow paths. Port and flow path 29 which is 0.1 inch ID serves reagent to the six two way valves 24 located on the rear of said manifold 25. With reference to FIGS. 12, 13 and 14; reagent is served to valve through flow paths 28 which is 0.062 inch ID through any valves that are turned on by system controller then distributed through flow path 27 which is 0.062 inch ID to flow path 30 which is 0.1 inch ID which distributes reagent to eight dispensing nozzles 34.

Flow path 31 which is 0.1 inch ID delivers reagents to six valves on the front of said manifold 25. Reagent is served to valves through flow paths 33 which is 0.062 inch ID through any valves that are turned on by system controller then distributed through flow path 32 which is 0.062 inch ID to flow path 30 which is 0.10 inch ID which distributes reagent to eight dispensing nozzles 34.

Reagent dispensing nozzles 34 are an integral part of the dispense manifold that significantly contribute to uniform flow across nozzles. Reagent dispense nozzles 34 are shown in detail in FIGS. 12 and 13. Reagent dispense nozzles 34 are secured to dispense manifold 25 using tube nuts 36 and ferrules 37. Reagent dispense nozzle 34 is PEEK tubing that is 1/32 inch OD×0.015 inch ID×1.2 inch long. Reagent dispense nozzle 34 is fitted into the center hole of a piece of Teflon tubing 35 that is 1/16 inch OD×0.030 inch ID×1.05 inch long. Teflon tube 35 is fitted into the center hole of a stainless steel tube that is 0.085 inch OD×0.072 inch ID×1.0 inch long. Stainless steel tube 39 provides support for dispense tube assembly.

In this embodiment, all ninety six dispensing nozzles are capable of dispensing a selectable volume of a selectable reagent onto as many as ninety six selectable reaction columns and the system controller is capable of sealing the chamber 60 above the reaction column 8 top openings and applying various pressures to the sealed chamber 60 thus forcing reagent to flow through the reaction columns 8 at a desired rate.

Figure 15:
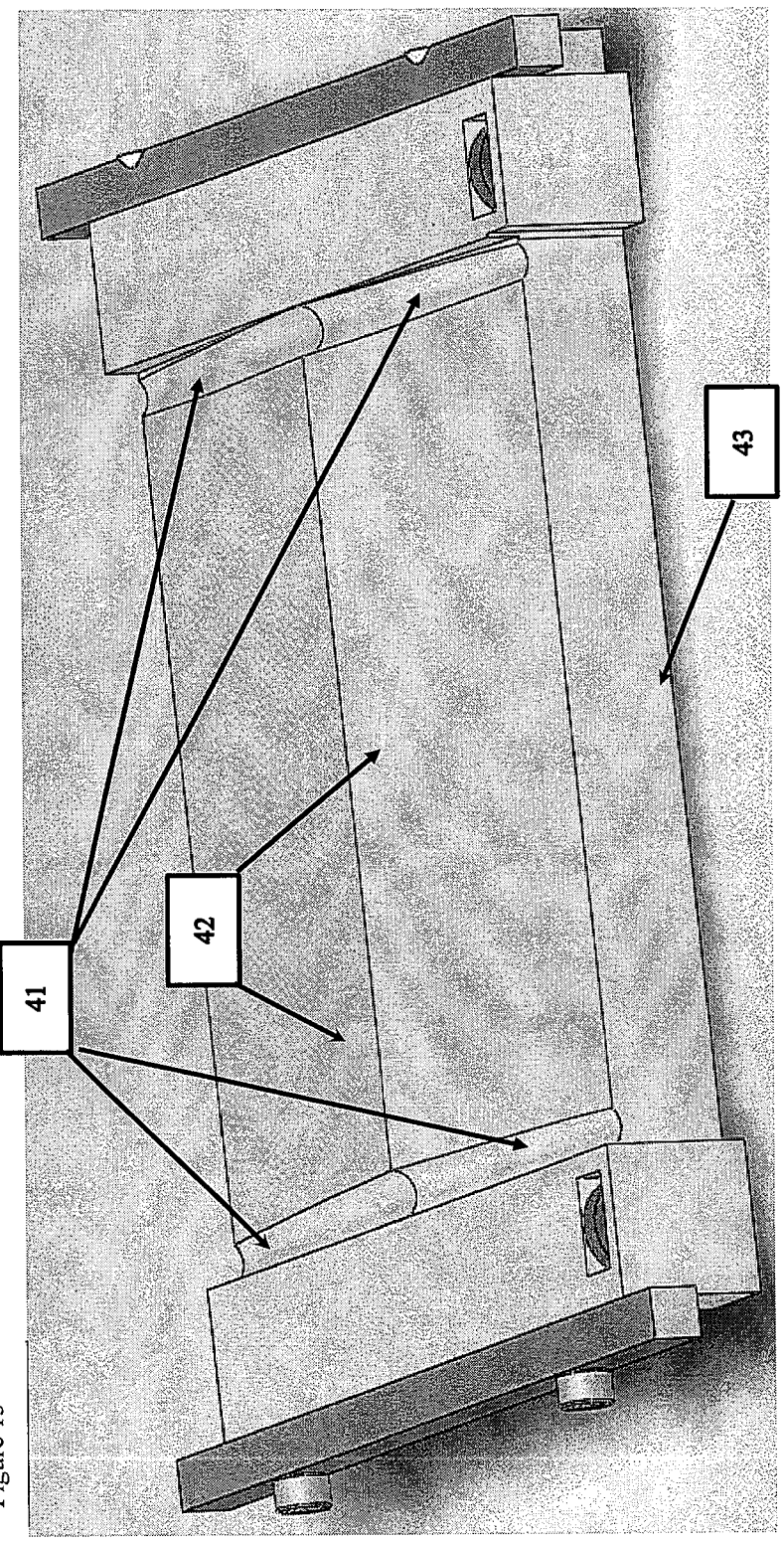
FIG. 15 is top perspective view of the cover plate which directs waste reagent around the tops of the collect containers.
Figure 16:
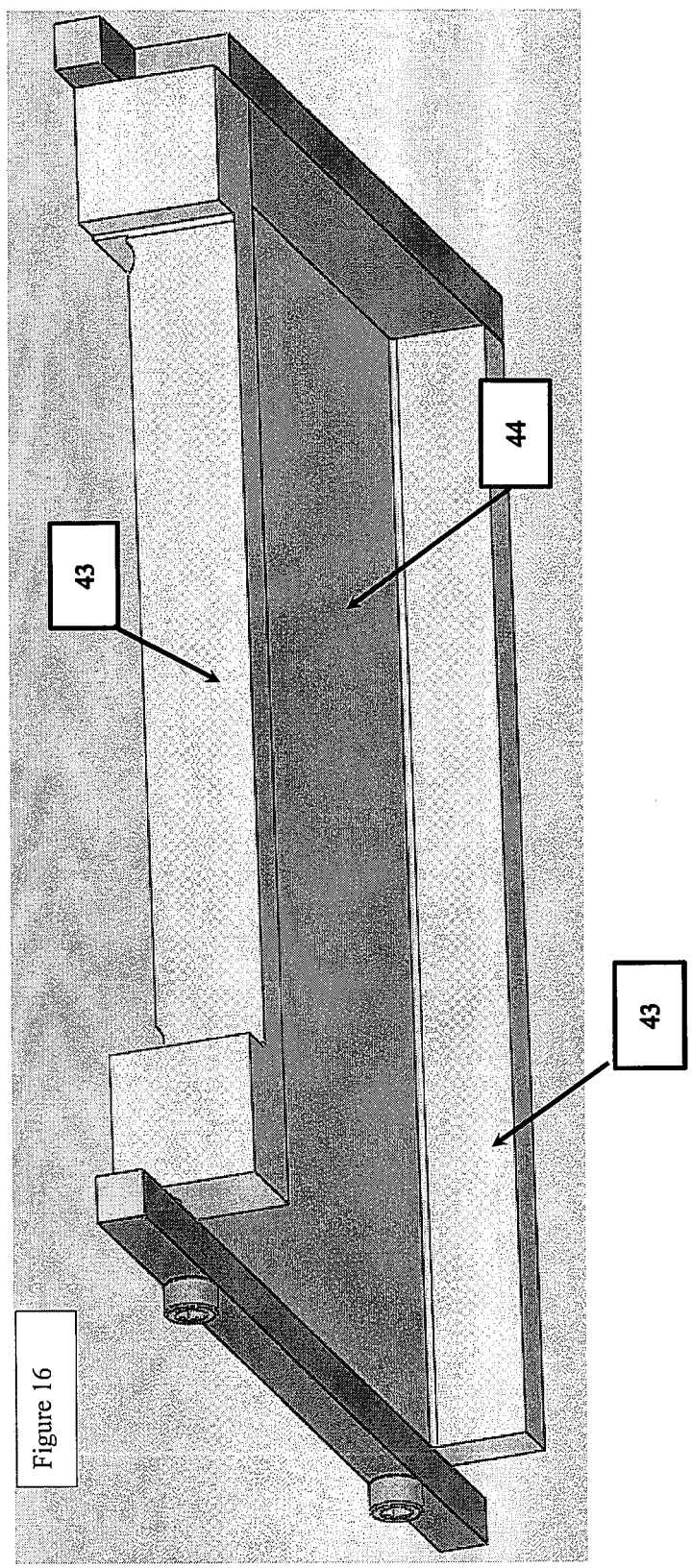
FIG. 16 is the bottom view of FIG. 15.

In addition to the sample transfer subsystem and reagent dispense subsystem, the instrument includes a means for directing reagent expelled from a matrix of reaction columns 8 either to waste or to a similar matrix of collect containers 40, as shown in FIGS. 15 and 16. A cover 38 that can be moved by shuttle 52 of FIG. 1 is movable between two locations. In a first location, cover 38 is positioned between outlets of the reaction columns and open tops of the wells of the collection containers. This diverts reagent expelled from reaction column outlets to waste. In second position, the cover is removed from between the outlets of the reaction columns and the wells of the collection containers to allow reagent expelled from reaction column outlets 47 to be collected in collection containers 40. Movable cover 38 top surface is fashioned as shown in FIG. 15 where in top surface 42 are sloping away from center to front and rear and wherein sloping troughs 41 are fashioned at left and right and flaps 43 are fashioned to hang over front and rear and protrude below open tops of collect containers 40. When cover is covering collection container openings collection container is slid into space 44 as shown in FIG. 16.

Liquid directed onto the top of the movable cover will flow off the front and rear edges. The extensions (43) insure the liquid flowing off the front and rear edges does not flow or move into the collection plate. The troughs catch liquid that may try to run off the left and right ends and keep it from going off the left and right ends. Liquid that hits to top of the cover is destined for waste. It flows into the large cavity which is below and is sent to a waste container by gravity through a tube.

Figure 19:
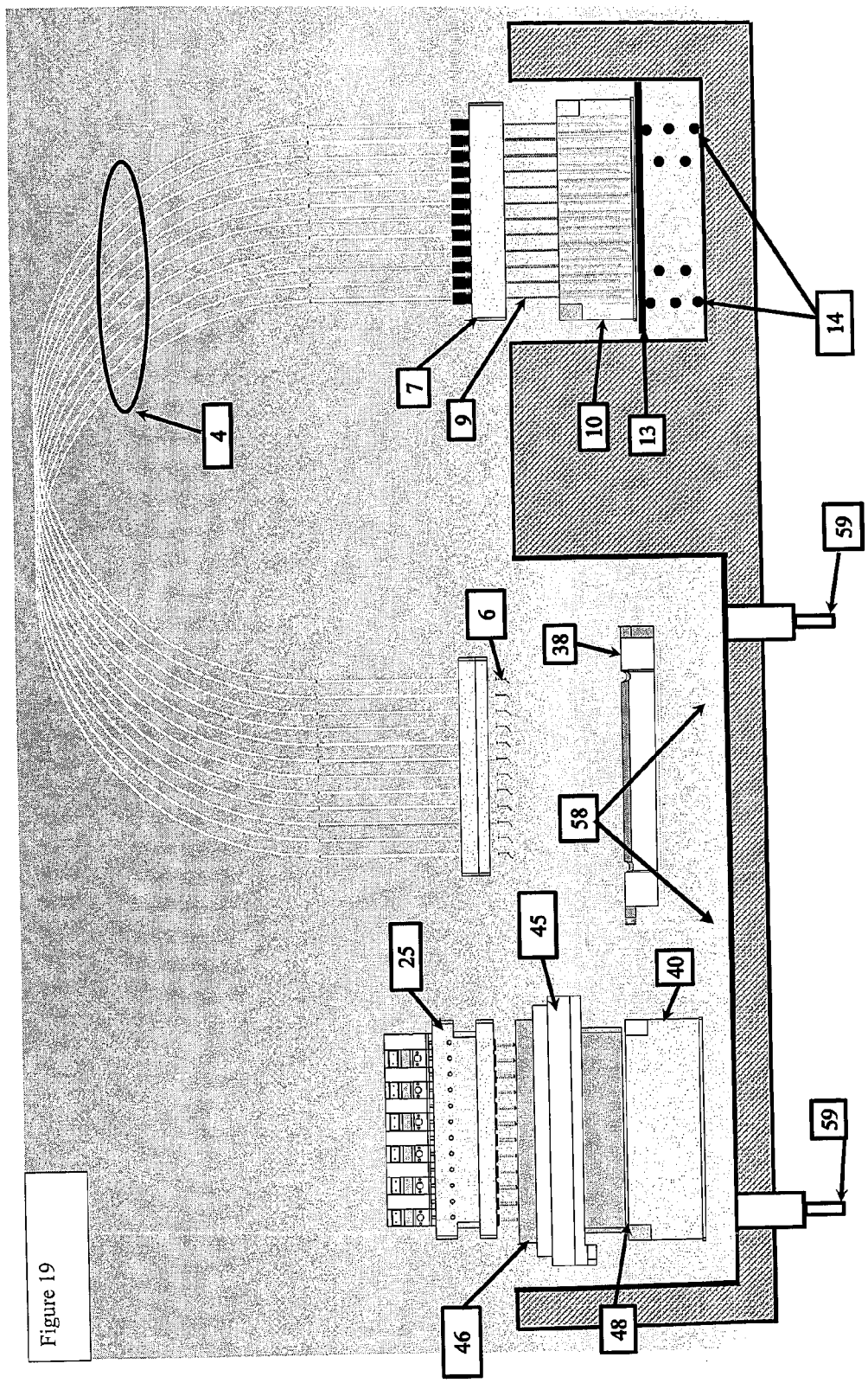
FIG. 19 is a front plan view showing the position of the components in the system when the transfer tubes are being washed and/or reagent in the reaction columns is being expelled to collect.

To FIG. 19 shows the lower waste cavity, which is a space that is drained to an external waste container through a waste tube 59. Waste is drained by gravity. There are two waste tubes 59 draining this space, one on left of the space and one on right of the space.

Figure 17:
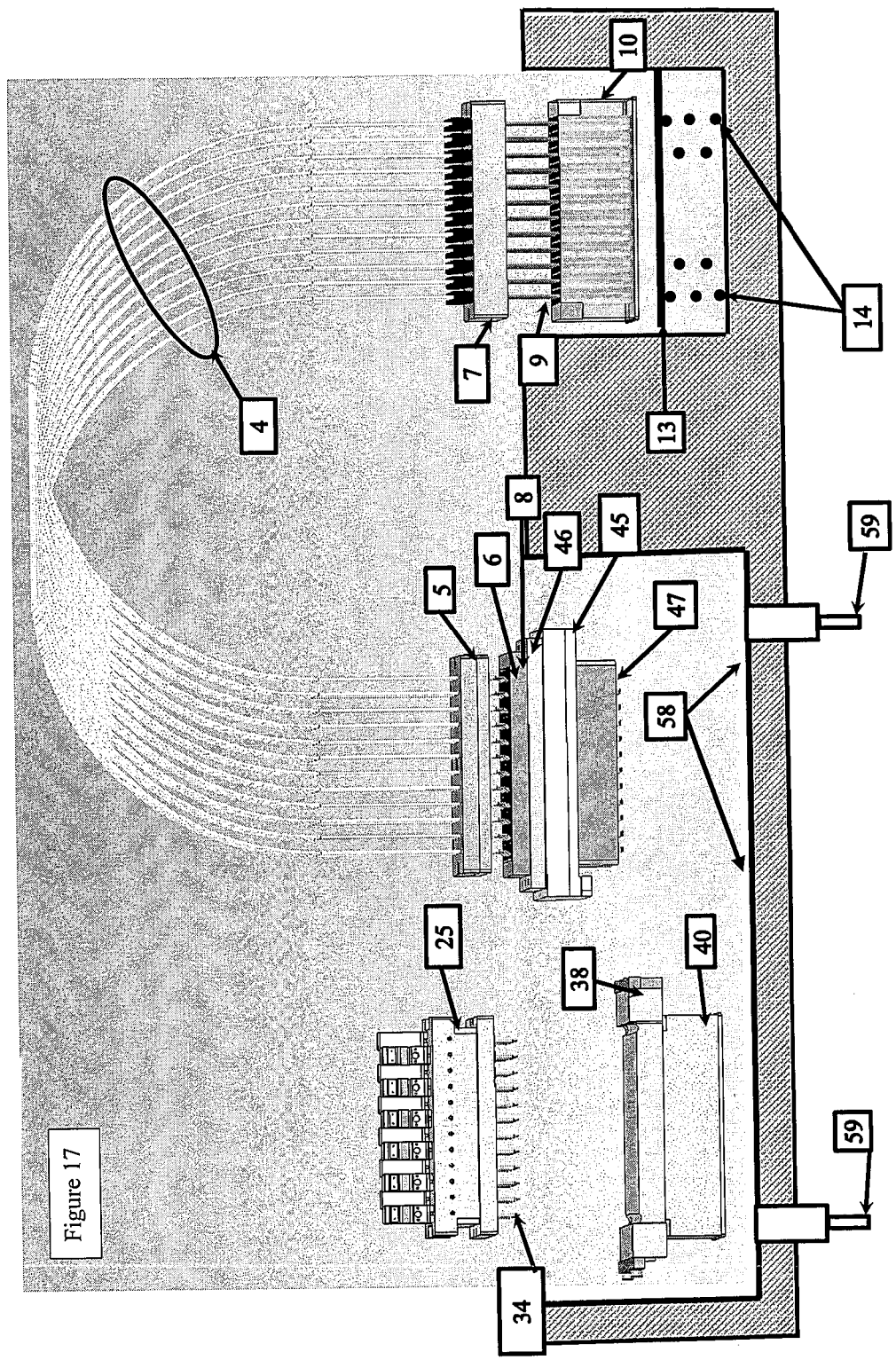
FIG. 17 is a plan front view showing the positions of components in the system when the reagent dispensing manifold is dispensing reagent to waste and/or samples are being transferred from the sample transfer containers to the reaction columns.

With reference to FIG. 17, the interworking of the components of the solid phase extraction system is illustrated. Housings around the components are not included for clarity.

Sample transfer system consists of ; Sample transfer container 10, sample transfer pickup tubes 9, sample transfer pickup manifold 7, sample transfer tubes 4, sample transfer dispense manifold 5 and sample transfer dispense nozzles 6.

FIG. 17 also shows the reaction column holder and associated parts which are; reaction column holder 46, reaction columns 8, reaction column holder cart 45 and reaction column outlet 47. Reaction columns 8 are shown in position for transferring samples to reaction columns. This is also the position reaction columns 8 are in when reagent dispense system 25 is priming to waste 58 and 59.

FIG. 17 shows Reagent Dispense Manifold Assembly 25. Reagents are dispensed from a matrix of as many as 96 dispense nozzles in reagent dispense manifold 25.

Cover 38 and collect containers 40 are shown directly beneath dispense manifold 25. In this position reagent dispense manifold nozzles 34 may be primed. Cover 38 is preventing reagent from being dispensed into collect containers 40 while diverting reagent to waste 58 and 59.

Figure 18:
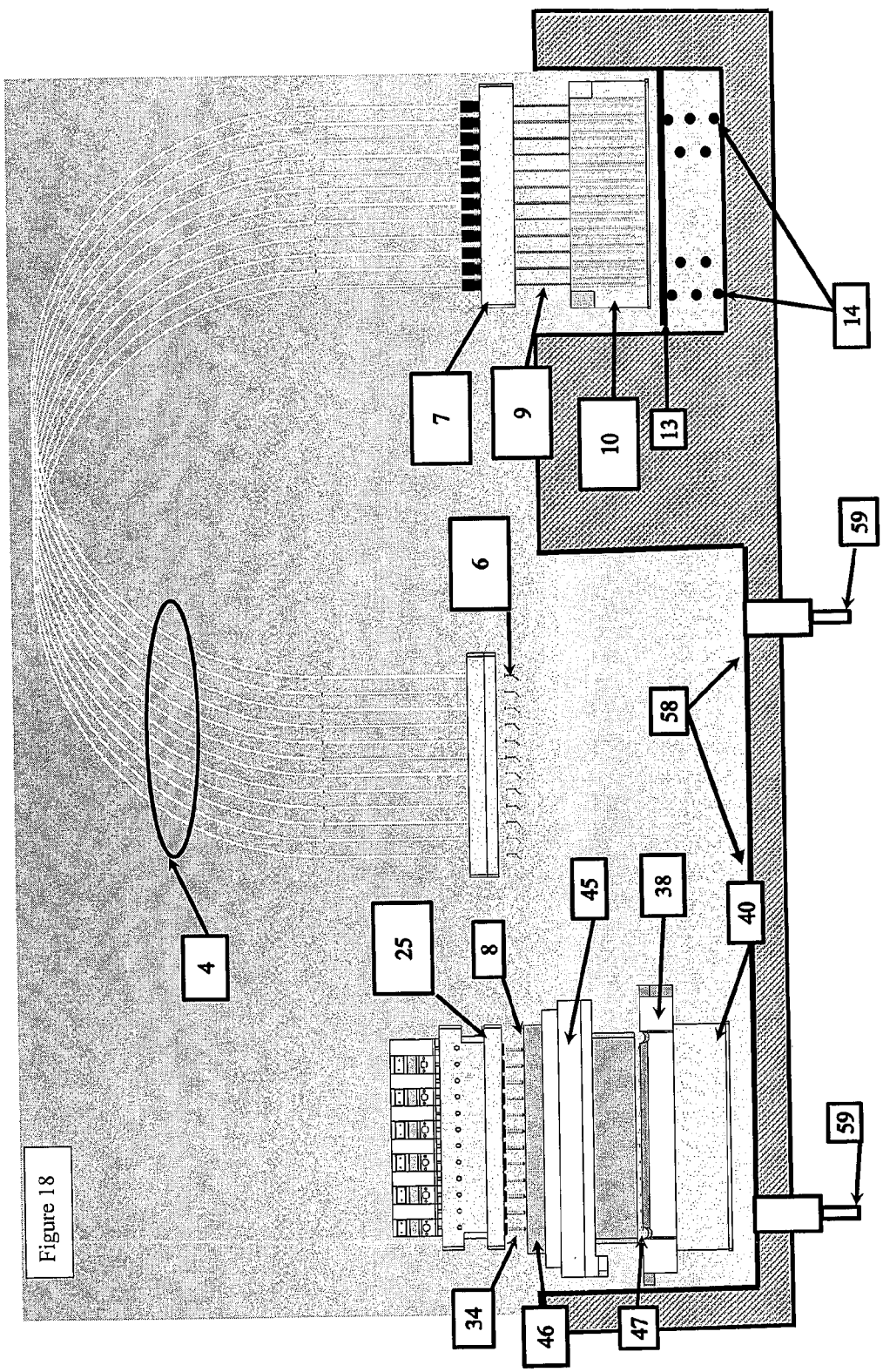
FIG. 18 is a plan front view showing the positions of the components in the system when the transfer tubes are being washed and/or the reagent dispensing system is dispensing reagent into the reaction columns and/or reagent in the reaction columns is being expelled to waste.

FIG. 18 shows reaction column holder 46 and reaction column holder cart 45 have been moved to the left placing reaction columns 8 directly beneath reagent dispensing manifold 25. Cover 38 is covering collect containers 40 preventing reagent expelled from reaction column outlets 47 from entering collect containers 40.

Transfer dispense nozzles 6 are over waste 58 and 59 allowing transfer tube assemblies 4 to be washed to waste.

FIG. 19 is showing the system with components in position for collecting product in collect container 40. Cover 38 is shown beneath transfer dispense nozzles 6. Reaction column outlets 48 are shown positioned inside tops of collect container. Buffer containing desired product is expelled from bottom of reaction columns 48 into collect container 40.

The control system and software that is facilitating automatic operation of the solid phase extraction system can utilize the various novel unique mechanisms of the invention to perform many different solid phase extraction process. A typical solid phase extraction process is illustrated. This example illustrates the system as used to perform purification of synthetically produced DNA fragments. Reaction columns designed for purification of synthetic DNA and sold by Glen Research Inc. Process followed was supplied by Glen Research Inc. Process can be organized into the following major steps:

1) Setup instrument for performing an automated extraction.
   a. Sample transfer container 10 is placed into sample transfer container chamber 57 as shown in FIG. 20.
   b. Reaction columns 8 is placed into reaction column holder 45 and reaction column holder 45 is placed into reaction column holder cart 46.
   c. A clean collect container 40 is placed into collect plate lift 54.

2) Prepare Reaction Columns
   a. Reaction columns 8 are moved to a position below reagent dispensing nozzles 34 shown in FIG. 20.
   b. Cover 38 is moved to a position to shield collect container 40 shown in FIG. 18.
   c. Desired volume of desired reagent is dispensed into active reaction columns 8.
   d. Gas pressure is applied to inlets of reaction columns 8 forcing reagent through reaction columns 8 to top of cover 34 which sheds reagent to waste.
   e. Steps 2c and 2d are repeated 2 times.

3) Transfer Sample to reaction columns
   a. Reaction columns 8 are moved to a position below transfer dispense nozzles 6 shown in FIG. 17.
   b. Gas pressure is applied to sample transfer chamber 57. Samples move through PEEK pickup tubes 9, through sample transfer tubes 4 and are dispensed into reaction columns 8 through sample transfer dispense nozzles 6 (As shown in FIG. 17).
   c. Reaction columns 8 is moved to a position below reagent dispensing nozzles 34 shown in FIG. 18.
   d. Gas pressure is applied to inlets of reaction columns 8 forcing sample buffer through reaction columns 8 to top of cover 34 which sheds reagent to waste. Sample is retained within reaction columns.
   e. Steps 3a thru 3d are repeated 4 times to transfer entire volume of sample buffer to reaction columns.

4) Wash reaction columns to remove contaminates
   a. Reaction columns 8 are moved to a position below reagent dispensing nozzles 34 shown in FIG. 20.
   b. Cover 38 is moved to a position to shield collect container 40 shown in FIG. 20.
   c. Desired volume of desired reagent is dispensed into reaction columns 8.
   d. Gas pressure is applied to inlets of reaction columns 8 forcing reagent through reaction columns 8 to top of cover 34 which sheds reagent to waste.
   e. Steps 4c and 4d are repeated 4 times.

5) Elute and collect product which is purified DNA fragments
   a. Reaction columns 8 are moved to a position below reagent dispensing nozzles 34 shown in FIG. 19.
   b. Cover 38 is moved to a position below sample transfer dispense nozzles as shown in FIG. 19 exposing reaction vessel outlets 48 to collect container 40 open tops.
   c. Collect Container 40 is moved up to engage outlets of reaction columns 48 into open tops of collect containers 40.
   d. Desired volume of sample elution buffer is dispensed into reaction columns 8.
   e. Gas pressure is applied to inlets of reaction columns 8 forcing reagent through reaction columns 8 to top of cover 34 which sheds reagent to waste.
   f. Steps 5d and 5e are repeated 2 times.

6) Wash Transfer System.
   a. Sample transfer container is filled with sample wash buffer.
      i. Sample wash buffer is flowed into sample transfer pickup manifold 7 through passages 22.
      ii. Sample wash buffer will flow down outside of PEEK pickup tubes 9 cleaning the outside and into sample transfer container 10 filling sample transfer container matrix of containers.
   b. Gas pressure is applied to sample transfer container 10. Wash buffer will flow through sample transfer pickup tubes 4 to waste through space 58 and waste tubes 59.

7) Process is complete, sample transfer container 10, reaction columns 8 and collection container 40 can be removed.

What is claimed is:

1. A system for automated solid phase extraction comprising:
   a transfer subsystem including:
      an array of pickup tubes;
      a spring mounted sample holding container platform configured to allow each of said pickup tubes to be controllably inserted to a selected depth of each well on a sample holding container held on said sample holding container platform;
      an array of transfer tubes contiguous with said array of pickup tubes;
      an array of transfer nozzles held in an equally spaced arrangement at terminal ends of said transfer tubes;
      a pressure controlled chamber enclosing and sealing said array of pickup tubes and said spring mounted sample holding container platform, configured to allow pressure driven fluid flow into said pickup tubes, through said transfer tubes and out said transfer nozzles; wherein application of pressure from a single source into said chamber is configured to drive fluid through all of said pickup tubes;
   a reaction column array shuttle configured to hold an array of equally spaced reaction columns and move said reaction columns from a first location, where said reaction columns are positioned to receive liquid dispensed from said transfer nozzles, to a second location;
   a dispense subsystem, separate from said transfer subsystem, including:
      a plurality of liquid distribution manifolds in spaced arrangement, each distribution manifold configured to selectably dispense liquid into a plurality of spaced dispense nozzles, wherein when said reaction columns are positioned at said second location, liquid may be dispensed through said reaction columns;
      a plurality of valves, each valve regulating fluid flow through one of said distribution manifolds; a collection plate lift configured to allow a multi well collection plate to be positioned such that liquid flowing through each reaction column is collected in a well of said collection plate;
      a waste collection cover positionable between open bottom ends of said spaced reaction columns and said collection plate;
      an automated controller configured to control said transfer subsystem and said dispense subsystem; and a waste collection cover shuttle configured to move said waste collection cover from a position where said waste collection cover is between outlets of said reaction columns when said reaction column array is in said second location, and openings of wells of said muiti well collection plate.

2. The system of claim one, wherein each pick up tube in said array of pick up tubes has a end that is partly cut away such that each tube has a flat section parallel to said sample holding container platform, and an angle cut such that when said flat section is pressed onto a surface, said angle cut section allows liquid to enter said pickup tube.

3. The system of claim one, wherein each pick up tube in said pick up tube array is made of PEEK.

4. The system of claim 1, wherein said transfer subsystem includes a guide plate through which said transfer tubes extend, said guide plate mounted on fixed rods, said guide plate maintaining a fixed spacing between said transfer tubes.

5. The system of claim 1, wherein said array of transfer nozzles includes an array of angled transfer nozzles, wherein each angle of each transfer nozzle is such that liquid flowing from said transfer nozzle into an associated reaction column is directed onto side walls of each reaction column.

6. The system of claim 1, wherein said spring mounted sample holding container platform includes a limit screw.

* * * * *